United States Patent
Theuerkauf et al.

(10) Patent No.: US 9,896,406 B2
(45) Date of Patent: Feb. 20, 2018

(54) METHOD FOR PRODUCING 2-METHYLBUTYRIC ACID HAVING A REDUCED CONTENT OF 3-METHYLBUTYRIC ACID FROM THE SECONDARY FLOWS ARISING IN THE PRODUCTION OF PENTANOIC ACIDS

(71) Applicant: Oxea GmbH, Oberhausen (DE)

(72) Inventors: Jens Theuerkauf, Krefeld (DE); Heinz Strutz, Moers (DE)

(73) Assignee: OXEA GMBH, Oberhausen (DE)

( * ) Notice: Subject to any disclaimer, the term of this patent is extended or adjusted under 35 U.S.C. 154(b) by 0 days.

(21) Appl. No.: 15/033,767

(22) PCT Filed: Nov. 14, 2014

(86) PCT No.: PCT/EP2014/003056
§ 371 (c)(1),
(2) Date: May 2, 2016

(87) PCT Pub. No.: WO2015/082043
PCT Pub. Date: Jun. 11, 2015

(65) Prior Publication Data
US 2016/0264503 A1   Sep. 15, 2016

(30) Foreign Application Priority Data

Dec. 5, 2013  (DE) .................. 10 2013 020 320

(51) Int. Cl.
| | |
|---|---|
| C07C 51/235 | (2006.01) |
| C07C 45/50 | (2006.01) |
| C07C 45/66 | (2006.01) |
| C07C 45/75 | (2006.01) |
| C07C 51/44 | (2006.01) |

(52) U.S. Cl.
CPC ............ C07C 51/235 (2013.01); C07C 45/50 (2013.01); C07C 45/66 (2013.01); C07C 45/75 (2013.01); C07C 51/44 (2013.01)

(58) Field of Classification Search
None
See application file for complete search history.

(56) References Cited

U.S. PATENT DOCUMENTS

| | | | |
|---|---|---|---|
| 4,599,206 A | 7/1986 | Billig et al. | |
| 4,950,800 A | 8/1990 | Weber et al. | |
| 5,026,920 A | 6/1991 | Roeper et al. | |
| 5,369,162 A | 11/1994 | Bahrmann et al. | |
| 5,463,147 A | 10/1995 | Bahrmann et al. | |
| 6,680,395 B2 | 1/2004 | Springer | |
| 6,800,783 B2 | 10/2004 | Springer et al. | |
| 7,799,945 B2 | 9/2010 | Springer | |
| 8,022,256 B2 * | 9/2011 | Caers ................ | C07C 29/141 |
| | | | 568/451 |
| 8,461,394 B2 | 6/2013 | Lueken et al. | |

FOREIGN PATENT DOCUMENTS

| | | |
|---|---|---|
| DE | 950007 | 10/1956 |
| DE | 2604545 A1 | 8/1977 |
| DE | 3744212 A1 | 7/1989 |
| DE | 3842186 A1 | 6/1990 |
| DE | 4210026 A1 | 9/1993 |
| DE | 4333324 A1 | 4/1995 |
| DE | 10010771 C1 | 5/2001 |
| DE | 10010770 C1 | 9/2001 |
| DE | 10108474 A1 | 9/2002 |
| DE | 10108475 A1 | 9/2002 |
| DE | 10225282 A1 | 12/2003 |
| DE | 102008002187 A1 | 12/2009 |
| EP | 0213639 A2 | 3/1987 |
| EP | 0366089 A2 | 5/1990 |
| EP | 1854778 A1 | 11/2007 |
| GB | 1565716 A | 4/1980 |
| WO | 2010117391 A1 | 10/2010 |

OTHER PUBLICATIONS

International Search Report dated Jan. 29, 2015.
Written Opinion dated Jan. 29, 2015.
International Preliminary Report on Patentability dated Jun. 9, 2016.

* cited by examiner

*Primary Examiner* — Clinton A Brooks
*Assistant Examiner* — Ana Z Muresan
(74) *Attorney, Agent, or Firm* — Michael W. Ferrell

(57) ABSTRACT

A process for preparing 2-methylbutyric acid having a reduced content of 3-methylbutyric acid from the secondary streams obtained in the preparation of pentanoic acids, includes generating a stream enriched with 2-methylbutanal and 3-methyl-butanal. The stream enriched with 2-methylbutanal and 3-methylbutanal of step is reacted with formaldehyde. The reaction with formaldehyde is followed by removal of the organic phase and selective hydrogenation in the presence of a hydrogenation catalyst with hydrogen at elevated temperature and elevated pressure and, after removal of the hydrogenation catalyst, treatment of the hydrogenation output obtained with an oxidizing agent.

20 Claims, No Drawings

METHOD FOR PRODUCING 2-METHYLBUTYRIC ACID HAVING A REDUCED CONTENT OF 3-METHYLBUTYRIC ACID FROM THE SECONDARY FLOWS ARISING IN THE PRODUCTION OF PENTANOIC ACIDS

CLAIM FOR PRIORITY

This application is a national phase application of PCT/EP2014/003056 FILED Nov. 14, 2014 which was based on application DE 10 2013 020 320.1 FILED Dec. 5, 2013. The priorities of PCT/EP2014/003056 and DE 10 2013 020 320.1 are hereby claimed and their disclosures incorporated herein by reference.

TECHNICAL FIELD

The present invention relates to a process for preparing 2-methylbutyric acid having a reduced content of 3-methylbutyric acid from secondary streams obtained in the preparation of pentanoic acids.

BACKGROUND

Pentanoic acids, also called valeric acids, have gained economic significance as intermediates in industrial organic chemistry. They occur in four different structural isomers as linear n-pentanoic acids, branched 2-methylbutyric acid, branched 3-methylbutyric acid and highly branched pivalic acid. Pentanoic acids can be used as such, for example for the production of fragrances. In addition, esters of pentanoic acids with polyols are finding increasing significance as lubricants. The pentanoic acids can be used in pure isomeric form or in the form of an isomer mixture (Weissermel, Arpe, Industrielle Organische Chemie [Industrial Organic Chemistry], 3rd edition, VCH Verlagsgesellschaft mbH, Weinheim, 1988, page 218; Schneidmeir, Chemiker-Zeitung, volume 96 (1972), no. 7, pages 383-387). The isomeric pentanoic acids are produced industrially by oxidation of the corresponding pentanals, or in the case of pivalic acid by hydrocarboxylation (Ullmann's Encyclopedia of Industrial Chemistry, 6th edition, 2003, Wiley-VCH Verlag GmbH & Co. KGaA, Weinheim, vol. 6, pages 495-503).

The pentanal starting compounds are prepared industrially by reaction of butenes with synthesis gas, a mixture of carbon monoxide and hydrogen, in the presence of transition metal compounds. The reaction of olefins with synthesis gas is also referred to as the hydroformylation reaction or oxo reaction, and the hydroformylation of but-1-ene affords, as well as the straight-chain n-aldehyde n-pentanal, also certain proportions of the isoaldehyde 2-methylbutanal (Ullmann's Encyclopedia of Industrial Chemistry, 6th edition, 2003, Wiley-VCH Verlag GmbH & Co. KGaA, Weinheim, vol. 2, pages 73-74; vol. 25, pages 286-289).

Butenes are obtained industrially by the steamcracking of naphtha. Typically, separation of 1,3-butadiene from the butene cut from the naphtha cracking to form raffinate I is followed by separation of isobutene to form raffinate II (Weissermel, Arpe, Industrielle Organische Chemie, 3rd edition, VCH Verlagsgesellschaft mbH, Weinheim, 1988, pages 71-79). For the subsequent hydroformylation reaction, predominantly raffinate II is used, in which a small residual isobutene content can be permitted. In special cases, it is also possible to process raffinate I having a high isobutene content, and occasionally also a but-1-ene-depleted raffinate II, which can also be referred to as raffinate III.

The hydroformylation reaction can be conducted either in the presence or in the absence of complex-forming compounds, for example in the presence of organophosphorus compounds. According to EP 0 366 089 A2, a homogeneous organic solution is employed with rhodium triphenylphosphine catalysis. Since a maximum proportion of n-pentanal compared to 2-methylbutanal in the pentanal mixture formed is generally the aim, the hydroformylation reaction is frequently conducted in the presence of homogeneously dissolved transition metal complexes, which first enable isomerization of the but-2-ene to but-1-ene, which is then hydroformylated predominantly to n-pentanal. Rhodium complex catalysts suitable for the isomerizing hydroformylation of a mixture of linear butenes are described, for example, in DE 102 25 282 A1, in which the complex ligands have a xanthene skeleton.

Rhodium complex catalysts based on bisphosphite ligands together with sterically hindered secondary amines, which are likewise suitable for the isomerizing hydroformylation of a mixture of linear butenes, are discussed in DE 10 2008 002 187 A1. Two-stage process variants are also known, for example according to DE 43 33 324 A1, DE 42 10 026 A1, DE 101 08 474 A1 and DE 101 08 475. In the first stage, preferably but-1-ene is converted, while, in the second stage, the but-2-ene-containing offgas from the first stage is hydroformylated to give a mixture of n-pentanal and 2-methylbutanal. According to DE 43 33 324 A1 and DE 101 08 474 A1, the first hydroformylation stage can also be conducted in the presence of water-soluble rhodium complex catalysts. In this type of reaction regime, a liquid aqueous catalyst solution is present alongside the liquid organic reaction solution, which, after leaving the hydroformylation zone, can be separated from one another in a simple manner by phase separation. Because of the presence of an aqueous phase and an organic liquid phase, this type of reaction regime is also referred to as a heterogeneous process or biphasic process.

According to the composition of the butene feed mixture and the reaction conditions in the hydroformylation stage, a pentanal mixture is obtained with varying proportions of n-pentanal, 2-methylbutanal, 3-methylbutanal and a small amount of pivalaldehyde, which is typically distilled. Because of the small difference in boiling point between 2-methylbutanal (92° C. at standard pressure) and 3-methylbutanal (92.5° C. at standard pressure), 3-methylbutanal cannot be separated completely from the 2-methylbutanal with acceptable distillation complexity and the 2-methylbutanal obtained is used for the preparation of 2-methylbutyric acid with a residual 3-methylbutanal content of typically greater than 0.2% by weight, based on the organic component. For particular applications, for example for fragrance production or for specific lubricants, however, there is a demand for a 2-methylbutyric acid quality where the residual 3-methylbutyric acid content has to be below 0.2% by weight, based on the organic component. A very low residual content of 3-methylbutyric acid below 0.2% by weight may also be important for n-pentanoic acid/2-methylbutyric acid mixtures. There is therefore a need for a process for preparing 2-methylbutyric acid having a reduced residual content of 3-methylbutyric acid from the secondary streams obtained in the preparation of pentanoic acids.

SUMMARY OF INVENTION

The present invention therefore consists in a process for preparing 2-methylbutyric acid having a reduced content of 3-methylbutyric acid from the secondary streams obtained in the preparation of pentanoic acids. It is characterized in that
   a) a mixture comprising linear butenes is reacted in the presence of transition metal compounds of group VIII of the Periodic Table of the Elements with carbon monoxide and hydrogen at elevated temperature and elevated pressure to give a pentanal mixture;
   b) the mixture obtained in step a) is separated into a stream enriched with 2-methylbutanal and 3-methylbutanal, and a stream enriched with n-pentanal;
   c) the stream enriched with 2-methylbutanal and 3-methylbutanal of step b) is reacted with formaldehyde;
   d) the reaction product obtained after step c) is treated with an oxidizing agent; and
   e) 2-methylbutyric acid having a residual 3-methylbutyric acid content of less than 0.2% by weight, based on the organic component, is removed by distillation from the reaction product obtained in step d),
with the proviso that the reaction with formaldehyde in step c) is followed by removal of the organic phase and selective hydrogenation in the presence of a hydrogenation catalyst with hydrogen at elevated temperature and elevated pressure and, after removal of the hydrogenation catalyst, treatment of the hydrogenation output obtained with an oxidizing agent in step d).

DETAILED DESCRIPTION

Feedstocks for the process of the invention are hydrocarbon mixtures typically containing very small amounts, if any, of polyunsaturated compounds and acetylene compounds and containing at least one of the olefins cis-but-2-ene, trans-but-2-ene and but-1-ene.

In addition, the feed mixture may include varying proportions of isobutene. Feed mixtures of this kind are industrially available as raffinate I, raffinate II or raffinate III.

The butene hydroformylation can be conducted in a homogeneous variant in the organic reaction medium with dissolved transition metal catalysts of group VIII of the Periodic Table of the Elements in the unmodified variant, or in the variant modified with complex ligands. Particularly effective solvents in the organic reaction medium have been found to be the higher-boiling condensation compounds of the pentanals, especially the trimers, which are obtained as by-products in the hydroformylation, and mixtures thereof with the pentanals to be prepared, and so a further addition to the solution is not absolutely necessary. In some cases, however, an additional solvent may be found to be appropriate. The solvents used are organic compounds in which starting material, reaction product and catalyst are soluble. Examples of such compounds are aromatic hydrocarbons such as toluene and benzene or the isomeric xylenes and mesitylene. Other commonly used solvents are paraffin oil, cyclohexane, n-hexane, n-heptane or n-octane, ethers such as tetrahydrofuran, ketones or Texanol® from Eastman. When the homogeneous variant in their presence is employed, suitable complex ligands are triarylphosphines such as triphenylphosphine (EP 0 366 089 A2), diphosphines, for example those based on the xanthene skeleton (DE 102 25 282 A1), phosphites as described, for example, in U.S. Pat. No. 4,599,206, or diphosphites, for example described in EP 0 213 639 A2 and DE 10 2008 002 187 A1. It is also possible to use mixtures of complex ligands, for example of triarylphosphines with phosphites or diphosphites, as known from WO 2010/117391 A1, in the hydroformylation reaction.

Through the choice of the composition of the butene feed mixture and the hydroformylation conditions, it is possible to control the ratio of n-pentanal to 2-methylbutanal.

If the aim is a maximum proportion of n-pentanal compared to 2-methylbutanal in the hydroformylation mixture, it is advisable, as well as a but-1-ene-rich feed stream, to use modified transition metal catalysts which at first bring about isomerization of the residual but-2-ene content to but-1-ene, which is then hydroformylated predominantly to n-pentanal. In one configuration of the process of the invention, it is possible to use the hydroformylation catalysts that are known from DE 102 25 282 A1 and have complex ligands based on the xanthene skeleton, or the hydroformylation catalysts that are known from EP 0 213 639 A2 or DE 10 2008 002 187 A1 and are based on sterically hindered diphosphites.

High proportions of n-pentanal can also be obtained in a two-stage process variant which is known per se from DE 101 08 474 A1 and DE 101 08 475. In the first stage, which can likewise be conducted by the heterogeneous variant in the presence of water with water-soluble complex ligands, for example with sulfonated phosphines such as triphenylphosphine with different degrees of sulfonation, predominantly but-1-ene reacts in high selectivity to give n-pentanal, and the but-2-ene-enriched offgas is subsequently converted in a second stage under isomerizing conditions to a pentanal mixture having a high n-pentanal content. By combining the streams from the first and second hydroformylation stages, it is possible to prepare a pentanal mixture having a high proportion of n-pentanal relative to 2-methylbutanal.

If the aim is a high proportion of 2-methylbutanal in the pentanal mixture, for example because of market circumstances, or said high proportion arises because of the composition of the butene feed mixture, preference is given to working in the absence of complex ligands in the unmodified mode of operation. In this case, the active hydroformylation catalyst forms from the transition metal or transition metal compound and carbon monoxide. It is assumed in the specialist literature that the transition metal compound $HM(CO)_4$ is the catalytically active transition metal species in the unmodified transition metal catalysis.

With increasing isobutene content in the butene feed mixture, the proportion of 3-methylbutanal in the hydroformylation product also increases.

In the modified variant, the molar ratio of transition metal to complex ligands is generally 1:1 to 1:1000, but it may also be higher. Preference is given to using the transition metal and the complex ligand in a molar ratio of 1:3 to 1:500, preferably 1:50 to 1:300. The modified hydroformylation reaction of the butene feed mixture is typically conducted at temperatures of 50 to 160° C. and pressures of 0.2 to 15 MPa. The transition metal concentration is generally 10 to 700 ppm, preferably 25 to 500 ppm, based on the reaction mixture.

If the unmodified variant is employed, the transition metal is used in smaller amounts, generally in an amount of 1 to 100 ppm, preferably 2 to 30 ppm, based on the amount of butene used. It is appropriate to work at higher pressures in the range from 5 to 70 MPa, preferably from 5 to 60 MPa and especially from 10 to 30 MPa. Suitable reaction temperatures vary within the range from 50 to 180° C., preferably from 50 to 150° C. and especially from 100 to 150° C.

The composition of the synthesis gas can be varied within wide limits. In general, mixtures in which the molar ratio of carbon monoxide and hydrogen is 5:1 to 1:5 are used. Typically, this ratio is 1:1 or deviates only slightly from this value in favor of hydrogen. The mixture comprising linear butenes can be supplied to the reaction zone as such or in solution with organic solvents, such as hydrocarbons.

The transition metals of group VIII of the Periodic Table of the Elements used are preferably cobalt, rhodium, iridium, nickel, palladium, platinum, iron or ruthenium, and especially rhodium and cobalt. The modified or unmodified transition metal catalyst forms under the conditions of the hydroformylation reaction from the transition metal compounds used, such as the salts thereof, such as chlorides, nitrates, sulfates, acetates, pentanoates or 2-ethylhexanoates, the chalcogenides thereof, such as oxides or sulfides, the carbonyl compounds thereof, such as $M_2(CO)_8$, $M_4(CO)_{12}$, $M_6(CO)_{16}$, $M_2(CO)_9$, $M_3(CO)_{12}$, the organo-transition metal compounds thereof, such as carbonyl acetylacetonates or cyclooctadienyl acetates or chlorides. It is possible here to use the transition metal compound in solid form or appropriately in solution. Particularly suitable transition metal compounds which are used as catalyst precursor are rhodium pentanoate, rhodium acetate, rhodium 2-ethylhexanoate or cobalt pentanoate, cobalt acetate or cobalt 2-ethylhexanoate or $Co_2(CO)_8$, $Co_4(CO)_{12}$, $Rh_2(CO)_8$, $Rh_4(CO)_{12}$ or $Rh_6(CO)_{16}$ or cyclopenta-dienylrhodium compounds, rhodium acetylacetonate or rhodium dicarbonyl acetylacetonate. Preference is given to using rhodium oxide and especially rhodium acetate, rhodium 2-ethylhexanoate and rhodium pentanoate.

Alternatively, it is also possible first to preform the transition metal catalyst in a pre-carbonylation stage and then to supply it to the actual hydroformylation stage. The preforming conditions generally correspond to the hydroformylation conditions.

The hydroformylation stage can be conducted either batchwise or continuously. The pentanal mixture formed is separated from the hydroformylation catalyst by conventional methods, for example by distillation in the homogeneous process regime or by simple phase separation from the aqueous catalyst solution in the heterogeneous or biphasic process regime.

The transition metal catalyst, optionally after addition of fresh transition metal compound and optionally fresh ligand if the modified mode of operation is being employed, and after removal of a portion of the aldehyde condensation products formed in the course of the reaction, is recycled into the reaction zone.

The requirement for a particular composition of the pentanal mixture obtained with regard to the n-pentanal, 2-methylbutanal and 3-methylbutanal isomers is guided by the market circumstances and can be controlled via the composition of the butene feed mixture and via the choice of the hydroformylation conditions. Frequently, the aim is a pentanal mixture containing generally at least 85 mol % of n-pentanal, less than 15 mol % of 2-methylbutanal and, depending on the isobutene content, less than 5 mol % of 3-methylbutanal, preferably less than 1 mol % and especially less than 0.2 mol % of 3-methylbutanal, based in each case on the sum total of pentanals. But pentanal mixtures having a higher proportion of 2-methylbutanal may also be demanded by the market.

The pentanal mixture obtained after the hydroformylation stage and after catalyst removal, which can also be regarded as crude hydroformylation product, is subsequently separated into a more volatile stream enriched with 2-methylbutanal and with 3-methylbutanal, and a less volatile stream enriched with n-pentanal, appropriately by distillation. The distillation of the crude hydroformylation product is effected by conventional methods in a distillation column. In order to obtain n-pentanal of maximum purity in the less volatile stream, the separation sharpness in the distillation is generally chosen such that the more volatile stream enriched with 2-methylbutanal and with 3-methylbutanal obtained likewise still contains amounts of n-pentanal. The exact composition thereof depends on the composition of the butene feed mixture, the hydroformylation conditions and the distillation conditions; for example, the composition of this volatile stream may be 80 to 85 mol % of 2-methyl-butanal, 10 to 14 mol % of n-pentanal and 1 to 10 mol % of 3-methylbutanal, based on the pentanal content. According to the isobutene content in the butene feed mixture, the 3-methylbutanal content may alternatively be higher or lower. In the less volatile stream, n-pentanal is concentrated in the virtual absence of the other pentanal isomers.

While n-pentanal having a boiling point of 103° C. at standard pressure can be separated from this volatile stream by a further conventional distillation in a further column having 10 to 100 trays as a product of high purity, 2-methylbutanal having a boiling point of 92° C. at standard pressure and 3-methylbutanal having a boiling point of 92.5° C. at standard pressure have too small a boiling point difference for sufficient separation with acceptable distillation complexity. This further distillation for n-pentanal removal can optionally be conducted.

According to the invention, the more volatile stream which is obtained after distillation of the crude hydroformylation product and has the main 2-methyl-butanal constituent and the residual 3-methylbutanal and n-pentanal contents is admixed with formaldehyde. The treatment of α-alkyl-substituted aldehydes with formaldehyde to remove residual amounts of aldehydes having two hydrogen atoms on the α-carbon atom relative to the carbonyl group in the course of purification is also referred to as the methylenation reaction and is known per se from the prior art and is described, for example, in DE 3842186 A1 and DE 3744212 A1.

The mixture comprising 2-methylbutanal, 3-methyl-butanal and n-pentanal is reacted with formaldehyde in the presence of an aldolization catalyst, typically a mixture of a secondary amine, for example an amine of the general formula $R^1$—NH—$R^2$ where $R^1$ and $R^2$ are the same or different and are each alkyl radicals having 1 to 12 and preferably 3 to 5 carbon atoms, and a monocarboxylic acid having 1 to 10 carbon atoms or a di- or polycarboxylic acid having 2 to 10 carbon atoms. Preference is given to using, as aldolization catalyst, a mixture of di-n-butylamine and n-butyric acid. However, other aldolization catalysts for the methylenation step are not ruled out. Formaldehyde is used in solid form, as paraformaldehyde, or appropriately as an aqueous solution in commercial concentration, such as 30% to 50% by weight, in which case the molar ratio of formaldehyde to the sum total of aldehydes having two hydrogen atoms on the α-carbon atom relative to the carbonyl group is 1 to 2.

The reaction is typically conducted at temperatures of 0 to 100° C. under autogenous pressure or slightly elevated pressure. Suitable reactors are the aggregates customary in chemical engineering, such as stirred tanks, stirred tank cascades, mixing pumps or flow tubes. Either a batchwise or a continuous reaction regime is possible. Flow tubes are particularly suitable for the continuous reaction regime, for example an upright or a horizontal flow tube or a multiply coiled flow tube. The flow tube may be operated as an empty tube, but it may likewise contain random packings or internals for intensive mixing of the organic phase with the aqueous phase, for example Raschig rings, saddles, Pall rings, helices, baffles or static mixers or mixer packings.

Static mixing elements are commercially available and are supplied, for example, in the form of Sulzer mixers or Kenicks mixers. An appropriate space velocity in the flow tube of the mixture of organic phase comprising 2-methylbutanal, 3-methylbutanal and n-pentanal and aqueous formaldehyde solution has been found to be from 0.1 to 10 $h^{-1}$, preferably from 0.1 to 5 $h^{-1}$ and especially from 0.1 to 3 $h^{-1}$, based on reactor volume and time.

The mixture leaving the reaction vessel is guided into a phase separator in which the organic phase is separated from the aqueous phase.

In the methylenation, formaldehyde and the secondary amine in the acidic medium at first form a Mannich salt which is preferably dehydrated with 3-methylbutanal and n-pentanal via the formation of the α-methylol derivative to give isopropylacrolein and n-propylacrolein, while 2-methylbutanal remains unchanged. Isopropylacrolein has a boiling point of 108.5° C. at standard pressure and n-propylacrolein boils at 117° C. at standard pressure, and both methylenation products can be separated from the 2-methylbutanal by distillation by conventional methods. The 3-methylbutanal content in the 2-methylbutanal removed is generally below 0.2% by weight, based on the organic component. This is optionally followed by another, fine distillation of the 2-methylbutanal.

The purified 2-methylbutanal obtained is subsequently oxidized to 2-methylbutyric acid. The oxidation of 2-methylbutanal is known per se (Ullmann's Encyclopedia of Industrial Chemistry, 6th edition, 2003, Wiley-VCH Verlag GmbH & Co. KGaA, Weinheim, vol. 6, pages 497-502) and is preferably conducted in the liquid phase, for example in tubular reactors provided with a distributor tray, although other process configurations such as oxidation in the gas phase are not ruled out. Suitable oxidizing agents are customary compounds suitable for oxidation of aliphatic aldehydes, such as oxygen, oxygen-containing gas mixtures, ozone, ozone-containing gas mixtures, peroxides, peracids, metal salts of peracids or transition metals in high oxidation states, for example potassium permanganate or manganese dioxide. Because of the good availability, oxidizing agents used are appropriately molecular oxygen or gas mixtures comprising molecular oxygen. Further constituents of such gas mixtures are inert gases, for example nitrogen, noble gases and carbon dioxide. The proportion of the inert constituents of the oxygen-containing gas mixture is up to 90% by volume, especially 30% to 80% by volume. The preferred oxidizing agents are oxygen or air.

The oxidation can be conducted either with addition of catalysts or in the absence of catalysts. Suitable catalysts are transition metals or compounds of transition metals, which may be added in small amounts, for example of 0.1 to 5 ppm, calculated as the transition metal and based on the aldehyde used, such as titanium, vanadium, chromium, molybdenum, manganese, iron, cobalt, nickel, ruthenium, rhodium, palladium or copper. Such a process regime is described, for example, in DE 100 10 771 C1 or DE 26 04 545 A1.

It is likewise possible to conduct the conversion in the presence of alkali metal or alkaline earth metal salts of weak acids. Especially in the case of oxidation of α-branched aldehydes in which the carbon atom adjacent to the carbonyl carbon atom bears the branch, the prior art recommends the presence of small amounts of alkali metal carboxylates to improve selectivity (DE 950 007, DE 100 10 771 C1). Appropriately, the oxidation is conducted in the presence of 1 to 30 mmol, preferably 1 to 15 mmol and especially 1 to 8 mmol per mole of aldehyde, calculated as alkali metal or alkaline earth metal. It is also possible to use a combination of alkali metal and alkaline earth metal carboxylates with transition metal compounds, as discussed in EP 1 854 778 A1.

It is not necessary to use the alkali metal or alkaline earth metal carboxylates in the form of a homogeneous compound. It is likewise possible to use mixtures of these compounds, although it is appropriate to use 2-methylbutyrates. Preference is given, however, to using homogeneous compounds, for example lithium 2-methylbutyrate, potassium 2-methylbutyrate, sodium 2-methylbutyrate, calcium 2-methylbutyrate or barium 2-methylbutyrate.

In general, a solution comprising alkali metal or alkaline earth metal 2-methylbutyrates is prepared by neutralizing an aqueous solution comprising alkali metal or alkaline earth metal compound with an excess of 2-methylbutyric acid and adding this solution to the 2-methylbutanal to be oxidized. Suitable alkali metal or alkaline earth metal compounds are particularly the hydroxides, carbonates or hydrogencarbonates.

Alternatively, it is possible to produce the alkali metal or alkaline earth metal 2-methylbutyrates in the reaction mixture by adding alkali metal or alkaline earth metal compounds which are converted under the reaction conditions to the 2-methylbutyrates. For example, it is possible to use alkali metal or alkaline earth metal hydroxides, carbonates, hydrogencarbonates or oxides in the oxidation reaction. They can be added either in solid form or as an aqueous solution.

The reaction with the oxidizing agent, preferably with oxygen or oxygen-containing gases, is conducted within a temperature range of 20 to 100° C. Preference is given to working between 20 and 80° C., especially between 40 and 80° C. The temperature regime, constant or variable temperature, can be matched to the individual requirements of the starting material and the circumstances of the reaction.

The conversion of the co-reactants is preferably effected at atmospheric pressure. However, the employment of elevated pressure is not ruled out. It is customary to work within a range from atmospheric pressure to 1.5 MPa, preferably at atmospheric pressure to 0.8 MPa.

The oxidation step can be conducted batchwise or continuously. Recycling of unconverted reaction participants is possible in both cases.

The acid obtained is subsequently distilled by distillation to give on-spec material. The purity of the 2-methylbutyric acid is generally above 99.7% by weight and the residual content of 3-methylbutyric acid is less than 0.2% by weight, based on the organic component. 2-Methylbutyric acid of this quality is outstandingly suitable as an acid component for the preparation of ester lubricants and fragrances.

In the process of the invention, after the reaction of the 2-methylbutanal- and 3-methyl-butanal-enriched volatile stream which likewise still contains residual amounts of n-pentanal with formaldehyde in the presence of the aldolization catalyst in step c), the organic phase is separated from the aqueous phase and the crude organic phase is selectively hydrogenated in the presence of a hydrogenation catalyst with hydrogen at elevated temperature and elevated pressure. This saturates the double bond in the α, β position relative to the carbonyl carbon atom with retention of the aldehyde group, such that the outcome of the selective hydrogenation is that a mixture comprising unchanged 2-methylbutanal, 2-methylpentanal from the selective hydrogenation of n-propylacrolein and 2,3-dimethylbutanal from the selective hydrogenation of isopropylacrolein is obtained. The selective hydrogenation is conducted in a known manner over supported or unsupported catalysts containing, as hydrogenation-active component, palladium, platinum, rhodium and/or nickel. Preference is given to working with palladium catalysts at temperatures of 120 to 180° C., preferably 140 to 160° C., and at a pressure of 1.5 to 5 MPa, preferably at 2 to 3 MPa.

The hydrogenation output obtained is optionally separated from the hydrogenation catalyst and then, optionally after removal of low and high boilers, oxidized. The oxidation conditions corresponding to the aforementioned conditions. What is obtained is a crude acid mixture which, as well as 2-methylbutyric acid, boiling point 177° C., also contains 2-methylpentanoic acid, boiling point 196° C., and 2,3-dimethylbutyric acid, boiling point 191° C., each at standard pressure. After distillation under conventional conditions, 2-methylbutyric acid is obtained with a purity of more than 99.7% by weight and with a residual 3-methylbutyric acid content of less than 0.2% by weight, based on the organic component.

In a configuration of the process of the invention, after the hydrogenation catalyst has been removed, the output from the selective hydrogenation is fractionally distilled. 2-Methylbutanal is separated as a more volatile component from the 2-methylpentanal and any 2,3-dimethylbutanal present. The aldehyde fractions separated were subsequently treated with an oxidizing agent under the conditions described above. After purification by distillation, 2-methylbutyric acid is obtained with a residual 3-methylbutyric acid content of less than 0.2% by weight, based on the organic component. 2-Methylpentanoic acid obtained as a separate fraction, which may likewise still contain 2,3-dimethylbutyric acid.

The process of the invention enables the preparation of 2-methylbutyric acid in high quality from secondary streams obtained in the preparation of pentanals. Because of the low residual 3-methylbutyric acid content, the 2-methylbutyric acid obtained is outstandingly suitable as an acid component in ester compounds. Ester compounds with lower monoalcohols are used for the production of fragrances, while ester compounds of polyols are used for the production of synthetic lubricants.

The high-purity 2-methylbutyric acid having a 3-methylbutyric acid content of less than 0.2% by weight can likewise be processed together with high-purity n-pentanoic acid to give a high-purity acid mixture which can also be referred to as isopentanoic acid.

The invention claimed is:

1. A process for preparing 2-methylbutyric acid having a reduced content of 3-methylbutyric acid from secondary streams obtained in the preparation of pentanoic acids, characterized in that
   a) a mixture comprising linear butenes is reacted in the presence of transition metal compounds of group VIII of the Periodic Table of the Elements with carbon monoxide and hydrogen at elevated temperature and elevated pressure to give a pentanal mixture;
   b) the mixture obtained in step a) is separated into a stream enriched with 2-methylbutanal and 3-methylbutanal, and a stream enriched with n-pentanal;
   c) the stream enriched with 2-methylbutanal and 3-methylbutanal of step b) is reacted with formaldehyde;
   d) the reaction product obtained after step c) is treated with an oxidizing agent; and
   e) 2-methylbutyric acid having a residual 3-methylbutyric acid content of less than 0.2% by weight, based on the organic component, is removed by distillation from the reaction product obtained in step d);
   with the proviso that the reaction with formaldehyde in step c) is followed by removal of the organic phase and selective hydrogenation in the presence of a hydrogenation catalyst with hydrogen at elevated temperature and elevated pressure and, after removal of the hydrogenation catalyst, treatment of the hydrogenation output obtained with an oxidizing agent in step d).

2. The process as claimed in claim 1, characterized in that the reaction with formaldehyde in step c) is effected in the presence of a secondary amine and a mono-, di- or polycarboxylic acid.

3. The process as claimed in claim 1, characterized in that, after removal of the hydrogenation catalyst, the hydrogenation output obtained is fractionally distilled and the separated fractions are treated with an oxidizing agent in step d).

4. The process as claimed in claim 1, characterized in that the secondary amine used is an alkylamine of the formula $R^1$—NH—$R^2$ where $R^1$ and $R^2$ are the same or different and are each alkyl radicals having 1 to 12 carbon atoms.

5. The process as claimed in claim 1, characterized in that a monocarboxylic acid having 1 to 10 carbon atoms or a di- or polycarboxylic acid having 2 to 10 carbon atoms is used.

6. The process as claimed in claim 1, characterized in that the oxidation in step d) is effected in the presence of alkali metal or alkaline earth metal carboxylates.

7. The process as claimed in claim 6, characterized in that the alkali metal or alkaline earth metal carboxylates used are lithium carboxylate, potassium carboxylate, sodium carboxylate, calcium carboxylate or barium carboxylate.

8. The process as claimed in claim 1, characterized in that oxidation is effected in the liquid phase in step d).

9. The process as claimed in claim 1, characterized in that the oxidizing agent used in step d) is oxygen or oxygen-containing gases.

10. The process as claimed in claim 1, characterized in that the reaction with formaldehyde in step c) is conducted continuously in a flow tube.

11. The process as claimed in claim 2, characterized in that the secondary amine used is an alkylamine of the formula $R^1$—NH—$R^2$ where $R^1$ and $R^2$ are the same or different and are each alkyl radicals having 1 to 12 carbon atoms.

12. The process as claimed in claim 3, characterized in that the secondary amine used is an alkylamine of the formula $R^1$—NH—$R^2$ where $R^1$ and $R^2$ are the same or different and are each alkyl radicals having 1 to 12 carbon atoms.

13. The process as claimed in claim 1, characterized in that the secondary amine used is an alkylamine of the formula $R^1$—NH—$R^2$ where $R^1$ and $R^2$ are the same or different and are each alkyl radicals having 3 to 5 carbon atoms.

14. The process as claimed in claim 2, characterized in that a monocarboxylic acid having 1 to 10 carbon atoms or a di- or polycarboxylic acid having 2 to 10 carbon atoms is used.

15. The process as claimed in claim 3, characterized in that a monocarboxylic acid having 1 to 10 carbon atoms or a di- or polycarboxylic acid having 2 to 10 carbon atoms is used.

16. The process as claimed in claim 4, characterized in that a monocarboxylic acid having 1 to 10 carbon atoms or a di- or polycarboxylic acid having 2 to 10 carbon atoms is used.

17. The process as claimed in claim 2, characterized in that the oxidation in step d) is effected in the presence of alkali metal or alkaline earth metal carboxylates.

18. The process as claimed in claim 3, characterized in that the oxidation in step d) is effected in the presence of alkali metal or alkaline earth metal carboxylates.

19. The process as claimed in claim 4, characterized in that the oxidation in step d) is effected in the presence of alkali metal or alkaline earth metal carboxylates.

20. The process as claimed in claim 5, characterized in that the oxidation in step d) is effected in the presence of alkali metal or alkaline earth metal carboxylates.

\* \* \* \* \*